United States Patent [19]

Dobson

[11] 4,242,189

[45] Dec. 30, 1980

[54] APPARATUS FOR MEASURING THE CONCENTRATIONS OF IONS

[75] Inventor: John V. Dobson, Hartlepool, England

[73] Assignee: National Research Development Corporation, London, England

[21] Appl. No.: 488,244

[22] Filed: Jul. 12, 1974

[51] Int. Cl.³ ............................................. G01N 27/46
[52] U.S. Cl. ............................ 204/195 R; 204/195 M; 204/195 F; 204/1 T
[58] Field of Search ............ 204/195 R, 195 F, 195 M

[56] References Cited

U.S. PATENT DOCUMENTS

| | | | |
|---|---|---|---|
| 2,882,212 | 4/1959 | Beard | 204/195 R |
| 2,886,497 | 5/1959 | Butler | 204/195 R |
| 3,258,414 | 6/1966 | Gregor et al. | 204/195 M |
| 3,357,903 | 12/1967 | Lawrence | 204/1 T |
| 3,498,900 | 3/1970 | Banks et al. | 204/195 R |
| 3,503,861 | 3/1970 | Volpe | 204/195 P |
| 3,649,473 | 3/1972 | Holden et al. | 204/195 R |
| 3,694,338 | 9/1972 | Weingarten | 204/195 F |
| 3,835,013 | 9/1974 | Grubb et al. | 204/195 R |

FOREIGN PATENT DOCUMENTS 397303 8/1933 United Kingdom .
1200595 7/1970 United Kingdom .
1304012 1/1973 United Kingdom .

OTHER PUBLICATIONS

Attar et al., Journal of Electroanalytical Chemistry and Interfacial Electrochemistry, 27, (1970), pp. 59–67.
Dobson et al., "The Palladium–Hydride Reference Electrode in Hydrogen–Free Electrolyte Solutions at Elected Temperatures", Reprint of Paper Presented at an International Conference at the University of Surrey in England, Jan. 1973.

Primary Examiner—T. Tung
Attorney, Agent, or Firm—Cushman, Darby & Cushman

[57] ABSTRACT

Equipment for measuring the concentration of certain ions, particularly hydrogen ions, is disclosed. The ion sensitive electrodes used in this equipment are far more stable than those previously available. Many of the electrodes described use palladium hydride as the ion sensitive electrode and the electrode is stabilized by monitoring the hydrogen concentration in the palladium and replenishing automatically when necessary.

18 Claims, 11 Drawing Figures

APPARATUS FOR MEASURING THE CONCENTRATIONS OF IONS

The present invention relates to ion selective electrodes which include metal hydrides, particularly but not exclusively palladium hydride, and to methods of ion concentration measurement using such electrodes.

The absorption of considerable quantities of hydrogen in palladium and some other metals to form alloys known as hydrides is well known. Palladium hydride retains hydrogen for a considerable time at room temperature; for example $\alpha+\beta$ palladium hydride electrode will remain in this phase for many days.

However, the rate of desorption increases greatly with temperature so that at temperatures above for example 150° C. the life of the $(\alpha+\beta)$ palladium hydride electrode is a few hours.

Provided the electrode is in the $(\alpha+\beta)$ phase, a palladium hydride electrode can be used to measure hydrogen ion concentration in aqueous solution because of its ideal Nernstian pH response in a way similar to the normal platinum-hydrogen electrode. Although the palladium hydride electrode is known, it has hitherto been considered as a laboratory curiosity because of its irreproducibility and limited life especially at high temperatures.

Further, where oxygen or reducible ions are present in solution some of these ions reach the surface of the electrode and cause an inaccurate electrode potential. Hence known palladium hydride electrodes cannot be used in these circumstances since they do not give a correct pH value.

According to a first aspect of the present invention there is provided apparatus for use in measuring the concentration of a particular ion in a liquid, comprising an ion selective electrode which includes a metal which forms a hydride, supply means for supplying hydrogen to the metal, and control means for so controlling the supply of hydrogen to the metal that the concentration of hydrogen in the metal is, in operation, maintained within a predetermined range such that the electrode potential remains constant when measured in a solution having a constant concentration of a particular ion.

One of the main advantages of the first and second aspects of the invention is the provision of an electrode with a very much extended, and probably indefinite life. The electrode, because the hydrogen concentration is maintained in the said range, is not affected by its previous history of use and requires only infrequent calibration. Glass electrodes on the other hand require constant recalibration and suffer from the effects of previous use.

In this specification the term ion selective electrode means an electrode whose potential in a solution measured relative to a reference potential, depends on the concentration of a particular ion, or a particular group of ions, in the solution.

Electrodes according to the invention may be used continuously at temperatures up to 250° C. in aqueous electrolyte, aqueous acid or alkali, including concentrated acid or alkali, whereas glass electrodes cannot be used above 150° C. even in dilute electrolytes even for short periods of time. Electrodes according to the invention may also be used in organic fused salt media and other non aqueous media.

If the pH value is to be measured the electrode may contain substantially only metal hydride although other substances which do not affect the selectivity of the electrode in relation to the hydrogen ion and which do not prevent the formation of a metal hydride may also be present.

The metal is preferably palladium, but other metals which can be used include yttrium, zirconium, titanium, vanadium, or alloys of palladium with one or more of these metals, or alloys of two or more of these metals.

If the concentration of another ion is to be measured, the metal, for example palladium, may be coated with a mixture of an acid and the salt of the acid which contains the ion the concentration of which is to be measured, provided that the acid and its salt are substantially not dissolved by the liquid in which the ion concentration is to be measured. For example the concentrations of the following ions: $Ca^{++}$, $Mg^{++}$, $Sr^{++}$, $Ba^{++}$, $Y^{++}$ and $La^{++}$ may be measured if, of course, a different electrode is provided for each ion. Each electrode includes a mixture of stearic acid and the salt of that acid with that ion, coating the palladium.

Preferably the acid and salt chosen for the mixture have a high melting point to allow the electrode to be used up to high temperatures.

According to a second aspect of the present invention there is provided an ion selective electrode for use in measuring the concentration of an ion in a predetermined solution or a predetermined group of solutions, including a metal hydride containing a proportion of hydrogen which allows electrode potential to remain constant for an interval sufficient for measurements to be made, and a coating for the metal hydride comprising a mixture of an acid and the salt of the acid with the ion, the concentration of which is to be measured, the acid and the salt being substantially insoluble in the predetermined liquid or group of liquids.

The supply of hydrogen, in the first and second aspects of the invention, may for example be electrolytic by the electrolysis, at intervals between ion concentration measurements, of the solution whose ion concentration is to be measured, or a different and separate electrolyte whose concentration is not being measured or the supply may be from a gas supply applied to part of the palladium which in operation is not immersed in the solution. The gas supply itself may include means for electrolysing a solution to provide hydrogen.

The control of the hydrogen supply may for example be at a steady rate such that the loss of hydrogen is substantially balanced, or monitoring means may be provided to determine the concentration of hydrogen in the palladium and the supply of hydrogen may be controlled in accordance with the output of the monitoring means either by controlling a rate of supply or by causing hydrogen to be supplied at intervals each time a low concentration limit is reached.

The monitoring means may measure the electrical resistance of the hydride in order to determine the concentration of hydrogen.

The said range of hydrogen concentration is preferably such that the hydrogen/palladium alloy remains in the $(\alpha+\beta)$ phase but operation in the $\beta$ phase is used for some electrodes.

The control means preferably includes means for applying a positive potential to the ion selective electrode with respect to a further electrode.

The positive pulses give rise to the following important advantages:

the electrode surface becomes self-cleaning since the pulses have the effect of liberating a small quantity of hydrogen from the palladium lattice and this hydrogen combines with the impurities or carries them away with it; and the effect of dissolved oxygen and reducible ions is practically eliminated since the hydrogen reacts with them and thus removes them.

Contamination with electrodes according to the invention is negligible since the only contaminant is a minute amount of hydrogen. Glass electrodes on the other hand cause contamination since $Na^+$, $K^+$, $Si^{4+}$ and other ions are leached from the glass and often have a serious effect on measurements.

Electrodes according to the invention may be used in solutions with solid suspensions since the self cleaning substantially prevents the fouling deterioration in performance and failure which occurs with glass electrodes.

Further electrodes according to the invention may be used in a system in which the electrolyte is flowing, that is it is constantly changed, or a system where the electrolyte static or flowing is open to the air so that oxygen becomes dissolved, or in a closed system where the electrolyte is static or flowing and continuous supplies of air are prevented from reaching the electrolyte.

Apparatus according to the first aspect of the invention may include an inert hollow elongated body with palladium wire forming the ion selective electrode wound round the outside of the body.

The inert body may contain a reference electrode provided a porous connection between the interior and exterior of the body exists.

The inert body may instead contain an auxiliary electrode and part of the palladium wire. When the interior is filled with a liquid which can be electrolysed to provide hydrogen, the concentration of hydrogen in the wire can be increased by connecting a d.c. electric power source between the wire and the auxiliary electrode.

The ion sensitive electrode may instead be a thick or thin walled tube of palladium or palladium silver alloy. With the thick walled tube, a cylinder of high pressure hydrogen may be connected to the interior by way of a valve which is operated to allow hydrogen to reach the interior when the hydrogen concentration becomes too low. For the thin walled tube, a tube connects to a container in which electrolysis to liberate hydrogen is carried out when the hydrogen concentration falls.

Certain embodiments of the invention will now be described by way of example with reference to the accompanying drawings in which.

Figure 1:
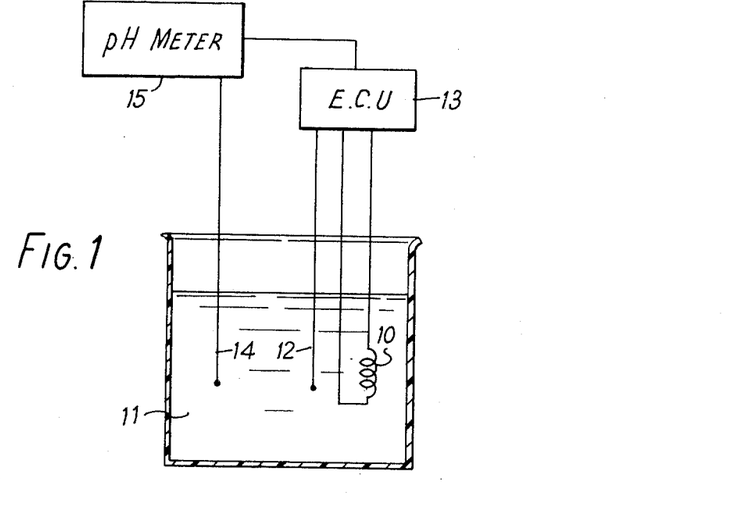
FIG. 1 is a block diagram of apparatus according to the invention.

In FIG. 1 a palladium wire electrode 10 is charged with hydrogen by the electrolysis of an electrolyte 11, the electrolysis being carried out between the palladium electrode 10 and an auxiliary platinum electrode 12. An electrical control unit 13 constantly measures the resistance of the palladium wire and in this way determines, as will be explained in more detail later, the concentration of hydrogen in the palladium. The control unit 13 causes electrolysis to take place when the desorption of hydrogen from the wire has reached a point when the palladium is about to leave the $(\alpha+\beta)$ phase.

Hydrogen ion concentration (pH value) measurements are carried out when electrolysis is not taking place by measuring the potential of the palladium wire electrode 10 with reference to the reference electrode 14 which may be, for example, a silver, silver chloride electrode. The potential of the electrode 10 depends upon the equilibrium between hydrogen in the alloy and hydrogen ions at the surface of the electrode and hence depends upon the hydrogen ion concentration of the electrolyte. The voltage between the electrodes 10 and 14 is measured by a pH meter (for example a specially graduated voltmeter) or digital voltmeter, or any other potential measuring device 15.

Figure 2:
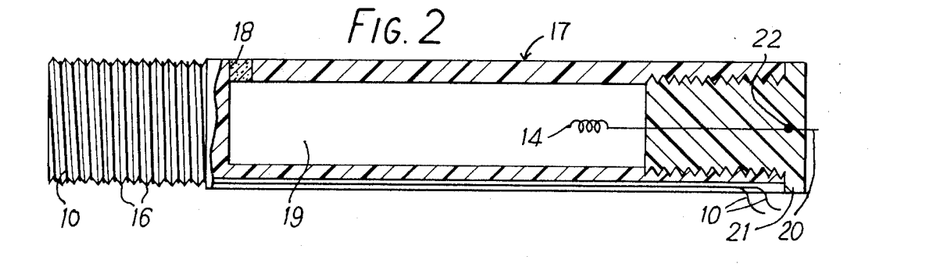
FIG. 2 is a schematic cross-section of a probe, which includes a palladium electrode and a reference electrode for use in the apparatus of FIG. 1.

One practical form of the palladium electrode 10 and the reference electrode 14 is shown in FIG. 2. Palladium wire forming the electrode 10 is wound round threads 16 formed on a hollow PTFE body 17. The wire is insulated where it runs along a groove in the body 17 to the upper end of the body (to the right of FIG. 2). The wire is also insulated where it returns over the thread from the lower end of the body to the groove. A sintered PFTE plug 18 forms a porous electrolyte connection between the electrolyte outside the body and that contained in a cylinder chamber 19 within the body. The chamber 19 also contains silver chloride fused to a silver wire 20 to form an electrode 14. The wire 20 passes through a screwed PTFE plug 21 by way of a bead electrical seal 22. The probe formed by the apparatus of FIG. 2 is used in an electrolyte whose pH value is to be measured and the chamber 19 is also filled with this electrolyte type although other electrolytes such as hydrochloric acid could be used.

Electrolytic cathodic charging is used to maintain the hydrogen concentration in the wire 16 in the correct range and for this purpose a platinum or some other inert electrode is also placed in the electrolyte. Clearly the probe of FIG. 2 can only be used with an electrolyte which can be electrolyzed to provide hydrogen. In addition the electrolyte must be flowing past the electrodes or be of large volume in order to prevent the electrolysis changing the pH value to be measured.

Figure 3:
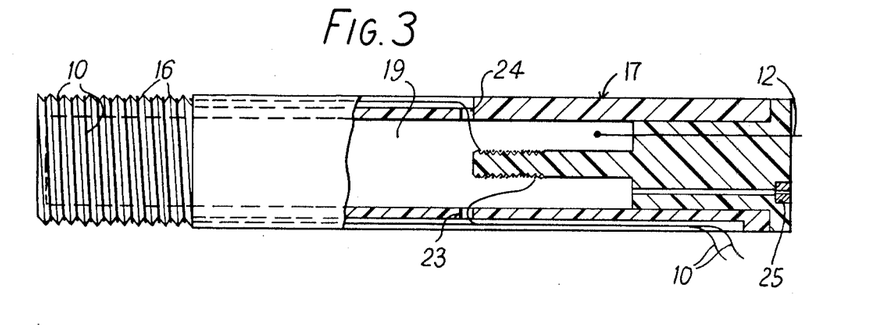
FIG. 3 is a schematic cross-section of a probe, for use with the apparatus of FIG. 1, which includes a palladium electrode, an electrolyte and an auxiliary electrode for charging the palladium electrode with hydrogen.

Another form of probe shown in FIG. 3 against has a palladium wire wound in threads 16 on the outside of a PTFE body 17 but in this case a palladium wire is taken in through seals 23 and 24 to the inner chamber 19 which in this case contains an electrolyte which can be electrolysed to provide hydrogen. As in FIG. 2 the wire is insulated where it is in grooves in the body between the thread, the seals 23 and 24, at the top of the probe, and the lower end of the thread.

Electrolysis to provide hydrogen is carried out between the wire 10 and the platinum wire 12 which is inside the chamber 19. A filler plug and air vent 25 is provided. The probe of FIG. 3 can thus be used with an electrolyte which cannot be electrolysed to provide hydrogen or an electrolyte which is not flowing, and in this case the reference electrode 14 (not shown in FIG. 3) is placed in the solution whose pH value is to be measured. The hydrogen liberated adjacent to that part of the wire 10 which is in the chamber 19 flows along the inside of the wire, in a way somewhat analogous to flow along a pipe, to maintain the required hydrogen concentration in that part of the wire which is wound on the exterior of the body 17. The wire 10 may in some cases be mainly within the chamber 19 with only a small portion on the outside of the body 17.

The electrical control unit 13 of FIG. 1 provides periodic anodic pulses between the electrodes 10 and 12 and these pulses "clean" the electrode in the way explained above. With the arrangement of FIG. 3 self-cleaning cannot be carried out by pulses between the auxiliary electrode 12 and the electrode 10, since the electrode 12 is in the chamber 19. Thus a separate auxiliary electrode is provided where cleaning is required.

Figures 4, 7, 10:
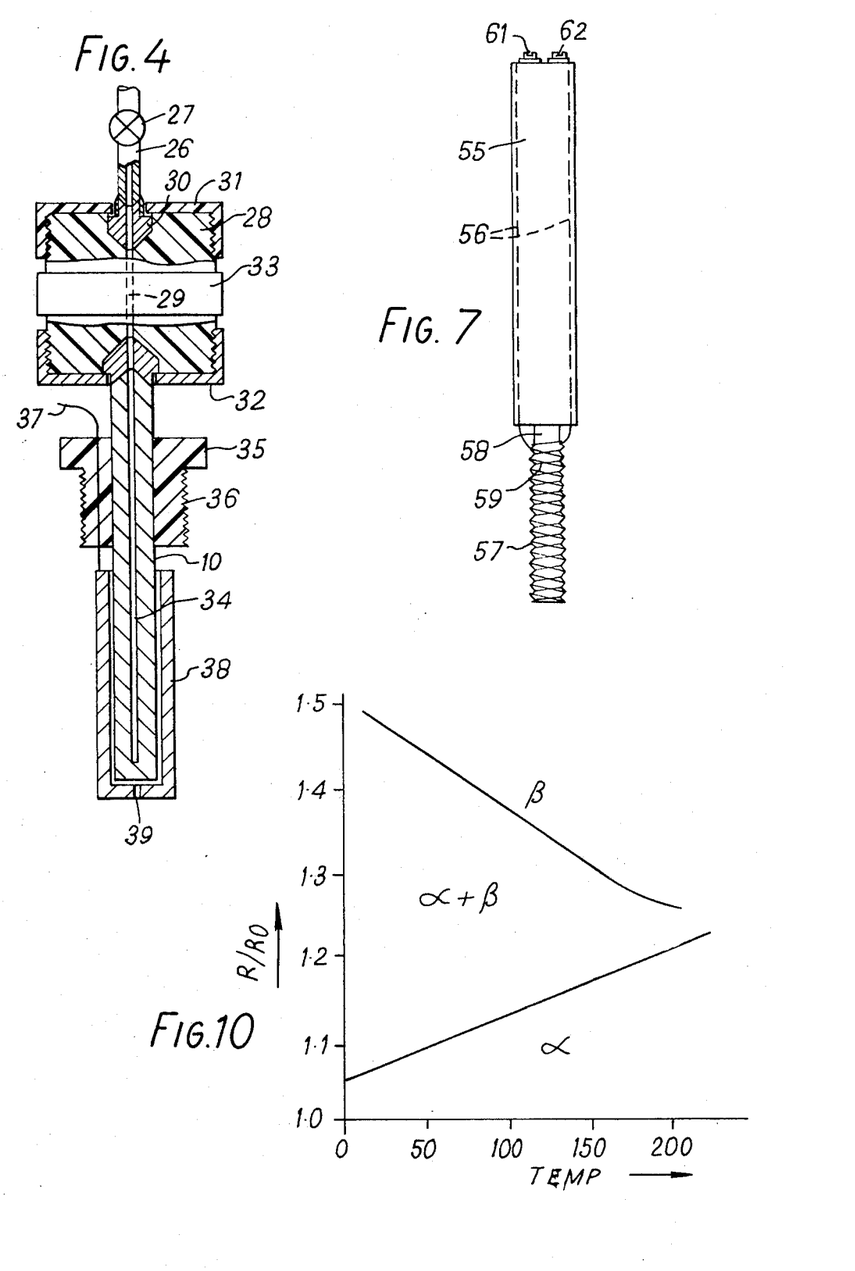
FIG. 4 is a schematic cross-section of a probe, for use in a modified form of the apparatus of FIG. 1, which has a palladium electrode with an internal chamber, and means for passing hydrogen into the chamber.
FIG. 7 is a schematic view of an ion selective electrode according to the third aspect of the invention.
FIG. 10 is a graph showing the relation between palladium hydride phases and the electrical resistance of palladium hydride.

In the form of the probe of FIG. 4 the hydrogen for the electrode is supplied through a copper or high pressure pipe 26 from a cylinder of hydrogen (not shown). In this case no auxiliary electrode 12 is provided since when hydrogen is required a valve 27 is opened by the control unit 13. A conical ended plug 30 is secured on to the copper pipe 26 and projects into a conical recess in a PTFE body 28 with a threaded exterior and a central bore 29. A brass cap 31 is screwed down on the PTFE body to make a firm connection between the pipe 26 and the body, and a similar joint between the body 28 and a silver palladium tube forming the electrode 10 is fixed firmly by a brass cap 32. A brass collar 33 surrounds the PTFE body 28 in order to strengthen it. Since the caps 31 and 32 are separated from the collar 33, the electrode 10 is electrically insulated from the pipe 26.

Figure 5:
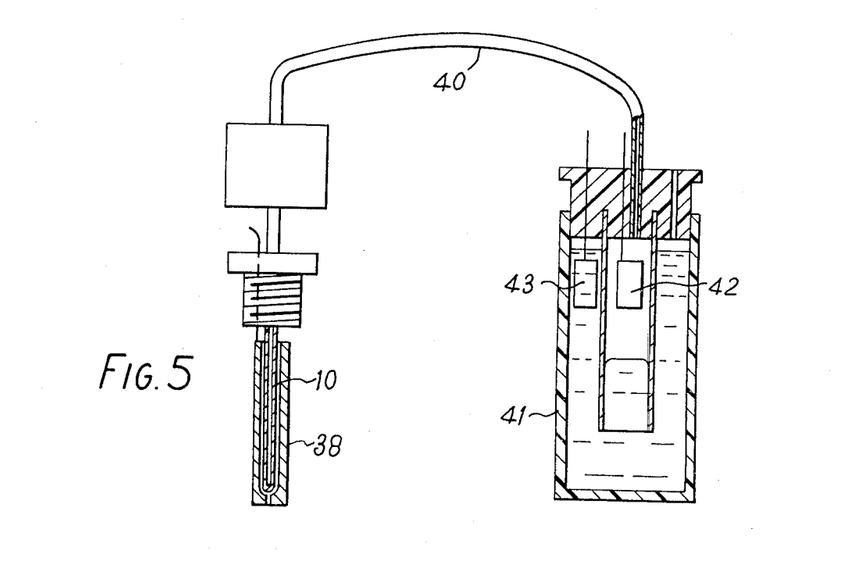
FIG. 5 is a schematic cross-section of a probe, for use in a modified form of the apparatus of FIG. 1, which has a palladium electrode with an internal chamber coupled to means for electrolysis to liberate hydrogen.

In FIG. 4 the electrode 10 is a silver/palladium alloy/rod with a small diameter bore 34 which connects through the bore 29 to the pipe 26. A PTFE plug 35, carrying a thread 36 allowing the probe to be screwed into a measurement cell, also holds a wire 37 which is connected to a platinum or palladium cylinder 38 fitted with a small intervening space round the electrode 10 throughout its length. Measurement of the potential between the electrode 10 and the cylinder 38 provides an indication of the concentration of hydrogen. Thus the control unit 13 functions, not by resistance measurement, but in this case by potential measurement. A small aperture 39 allows the electrolyte to circulate freely between the electrode 10 and the cylinder 38.

Where the use of a high pressure gas supply is not appropriate, the apparatus of FIG. 5 may be used. This comprises a thin walled palladium/silver alloy membrane forming the electrode 10. This membrane in tubular form is connected to a pipe 40 by the same type of insulating connector as is shown in FIG. 4. The pipe 40 enters a PTFE container 41 containing an electrolyte which can be electrolysed to liberate hydrogen when current is passed between a platinum electrode 42 and a further platinum electrode 43. The control unit 13 causes electrolysis to be carried out in the container 41 when potential measurements between the cylinder 38 and the electrode 10 indicate that the hydrogen concentration in the membrane 10 is low. As before a space exists between the cylinder 38 and the electrode 10 allowing electrolyte to circulate freely.

As electrolysis proceeds the hydrogen released pushes the electrolyte level down in the region of the electrode 42 as shown. Electrolysis then ceases until the hydrogen has sufficiently desorbed from the electrode 10 for the electrolyte level to rise again. Thus a regulating mechanism is set up which may possibly be used instead of the control unit 13 but preferably in addition to the unit 13.

The electrodes of FIGS. 4 and 5 may be modified for control by resistance measurement by making the walls of the electrode 10 (with its internal bore) from alternate strips of PTFE and palladium; that is, viewed in horizontal cross-section, arcs of palladium are separated by arcs of PTFE. The low resistance of the electrode is increased by connecting the palladium strips in series and the cylinder 38 is no longer required.

Figure 6:
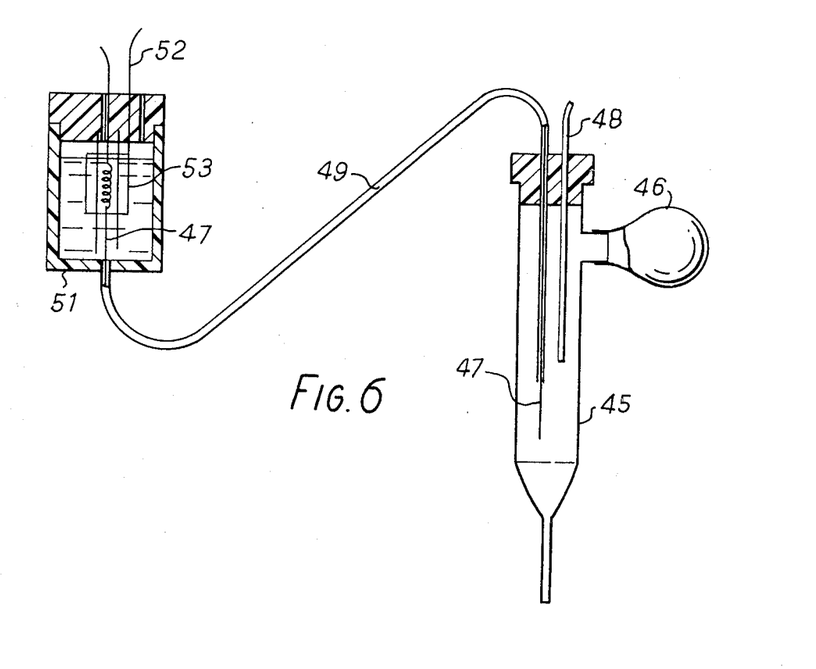
FIG. 6 is a schematic cross-section of a palladium hydride electrode for medical or biological applications.

An example of a form of a palladium hydride electrode in which the hydrogen concentration is not monitored is shown in FIG. 6. Here a glass container 45 with a rubber teat 46 contains a palladium wire electrode 47. The apparatus of FIG. 6 is used for biological or medical purposes and the liquid whose pH value is to be measured is drawn into the container 45 using the teat. A cannela 48 filled with electrolyte connects the interior of the container 45 to a reference electrode. The wire 47 is surrounded by fine bore PTFE flexible tubing 49 which projects for some distance into the container 45 and also protects the wire between the container 45 and a further PTFE container 51. In addition the tube 49 prevents loss of hydrogen along the wire 47. The palladium wire 47 extends the top of the container 51 as does a platinum wire 52 which is connected to a platinum cylinder 53. A small battery (not shown) is connected between the wires 47 and 52 and electrolysis of an electrolyte is carried out continuously to liberate hydrogen and allow it to be absorbed by the wire 47 at a rate substantially equal to desorption from the wire along its full length but mainly in the container 45. Vents are provided to allow oxygen to escape from the container 51. Thus in the arrangement of FIG. 6 the hydrogen concentration is constantly maintained at the required level by the constant absorption of hydrogen in the container 51. Potential measurements for pH value are, of course, made between the wire 47 and the reference electrode.

In addition to its use for measuring pH values, the present inventor has found that the palladium hydride electrode can be used to measure the concentrations of some other ions. For example the palladium hydride electrode can be made responsive to calcium, magnesium, strontium, barium and yttrium ions in an aqueous electrolyte if the palladium wire or palladium cylinder is coated with a mixture of a fatty acid and its salt of the ion whose concentration is required.

An ion selective electrode responsive to calcium is shown in FIG. 7 where a solid PTFE body 55 has longitudinal grooves 56, and threads 57 cut in a portion 58 of reduced diameter. A thin coating of melted mixture of 50% stearic acid and 50% calcium stearate is applied by way of brush to the PTFE former. The threads cut into the PTFE former and help to retain the mixture when cold. A palladium wire 59 is then wound from a screw 61 along the threads and back up over the portion 58 diagonally to the threads and back along the grooves 56 to a screw 62. The mixture is then used to coat the palladium wire at the intersections where the "go" and "return" wires cross but other portions of the palladium wire are left exposed. However, the wire is wound under tension so that the main part of the wire is embedded in the mixture. The control unit 13 is used to measure the resistance of the wire and the wire can be charged with hydrogen by electrolysis in the way previously described through those parts of the wire which are not covered with the mixture.

Such an ion selective electrode can be made sensitive to other ions simply by using other stearates, having the appropriate ion instead of calcium in the mixture.

The electrodes of FIGS. 2 and 4 to 6 can also be made selective to other ions by use of such a mixture, as can that of FIG. 3 but in the arrangement of FIG. 3 the wire can be entirely coated with a mixture where it is on the exterior of the body 70.

The operation of ion selective electrodes based on glass electrodes is described in a paper by Attar and Beck entitled "Alkaline Earth and Lanthanum Ion Electrodes of the Third Kind based on the Hydrogen Ion-Responsive Glass Electrode", published in the Journal of Electro-analytical Chemistry and Interfacial Electrochemistry, 27,(1970) pages 59–67. It is thought that the palladium hydride electrode when coated with one of the above mentioned mixtures operates in a way which is analogous to the ion selective electrodes of the above paper.

Figures 8A, 8B:
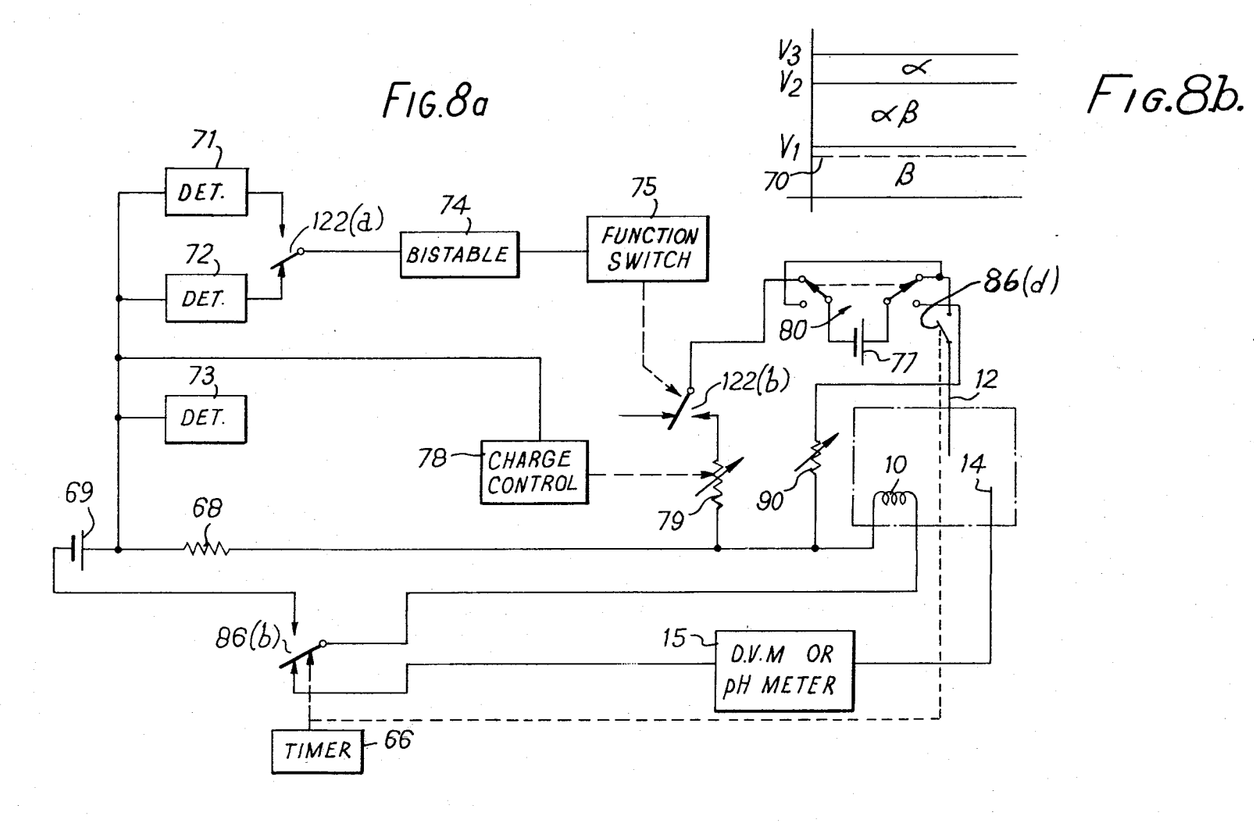
FIG. 8(a) is a block diagram of the electrical control unit of FIG. 1.
FIG. 8(b) is a graph illustrating the triggering voltages of detector circuits of FIG. 8(a)

The electrical control unit 13 will now be described in more detail. In FIG. 8a the palladium wire electrode 10 is connected through relay contacts 86(a) to the D.V.M. or pH meter 15, the other side of which is connected to the reference electrode 14. The operation of the contacts 86(b) is under the control of a sequential timer 66. The timer operates to connect the D.V.M. for, for example, three minutes and then to disconnect the meter for ten seconds. This cycle is continually repeated to alternately allow pH measurement and the measurement of the resistance of the palladium wire.

The contacts 86(b) in their other position complete the circuit for measuring the resistance of the palladium, these contacts being connected in series with the palladium wire electrode 10, a resistor 68 and a battery 69. Since the voltage across the resistor 68 depends on the current from the battery 69, this voltage indicates the resistance of the palladium wire electrode 10. The voltage across the resistor 68 is applied to three detector circuits 71, 72 and 73. Where the electrodes of FIGS. 4 and 5, or similar electrodes, are used, the resistor 68 and the battery 69 are not required. The voltage between the electrode 10 and the cylinder 38 is applied to the detectors 71, 72 and 73 by way of the contacts 86(b).

The detector 72 provides an output voltage when the voltage across the resistor 68 falls below a voltage $V_1$ (see FIG.8(b)) just above the boundary 70 between the $\beta$ and the $\alpha\beta$ phases, indicating that the palladium is about to enter the $\beta$ phase. As the voltage across the resistor 68 rises it is an indication first that the palladium has entered the $(\alpha+\beta)$ phase and as the voltage rises further that it has entered the $\alpha$ phase. The $\alpha$ phase is the phase in which the palladium contains insufficient hydrogen for a steady potential and the $(\alpha+\beta)$ phase is the phase in which the electrode should operate.

The detector 72 is set to provide an output signal when a voltage $V_2$ (see FIG. 8(b)) is reached that is when the palladium hydride enters the $\alpha$ phase from the $(\alpha+\beta)$ phase.

The detector 73 provides an output signal when the voltage across the resistor 68 rises to $V_3$ indicating that the palladium hydride has already entered the $\alpha$ phase and the system is now out of limits of useful operation.

The outputs of the detectors 71 and 72 are connected to contacts (122(a)) of a relay operated by the output of a bistable circuit 74. Thus is the detector 71 is connected to the bistable circuit 74 through the contacts 122(a) and the detector 71 operates, then the contacts 122(a) connect the detector 72 to the bistable circuit 74. When the voltage $V_2$ is exceeded the detector 71 once more becomes connected to the bistable 74. When the detector 71 has just operated, the bistable circuit enters a state in which a function switch 75 operates an indicator lamp indicating that the palladium is in the $\beta$ phase. When the detector 72 has just operated the bistable circuit enters its other state in which the function switch 75 operates contacts 122(b) connecting an electrical source 77 shown in FIG. 8(a) as a battery to the palladium electrode 10 so that current passes between the electrode 10 and the auxiliary electrode 12 charging the palladium hydride with hydrogen. At the same time a lamp connected to the function switch 75 indicates that charging is taking place further relay contacts 86(d) controlled by the timer 66 prevent electrolysis taking place when the measuring device 15 is connected to the contacts 86(d).

The detector 73 lights a warning lamp when the voltage $V_3$ is exceeded as an indication that the rate of charging may not be sufficient to make up hydrogen loss and should be increased.

The connection of the battery 77 is by way of a six pole reversing switch 80 which allows positive pulses for cleaning the electrode 10 to be generated manually when required. A variable resistor 90 allows the cleaning current which flows in the opposite direction to the charging current to be adjusted.

A transistor shown in FIG. 8a as a variable resistor 79 is controlled by a circuit 78 to adjust the rate of charging between the electrodes 10 and 12 in dependence upon the rate of loss of hydrogen. The rate of loss is sensed by differentiating the voltage across the resistor 68.

The $(\alpha+\beta)$ phase extends over a reduced range of hydrogen concentration in palladium as temperature rises. Thus although the change in resistance of palladium with hydrogen concentration is nearly linear throughout most of the range of interest the voltages which the detectors 71, 72 and 73 operate should be set with the temperature range of operation of the electrode in mind.

FIG. 10 is a graph showing the boundaries of the $\alpha$, $\beta$ and $(\alpha+\beta)$ phases in terms of the normalised palladium wire resistance $R/R_o$, $R_o$ being the resistance of a palladium wire which does not contain hydrogen.

A typical sequence of operation is as follows assuming that the sequence starts with the hydride in the $\beta$ phase, the detector 71 operated, and therefore with the detector 72 connected to the bistable circuit 74. As the hydrogen desorps, the hydride passes into the $(\alpha+\beta)$ phase allowing measurements to be made, and then into the $\alpha$ phase when the detector 72 operates. Charging now begins and continues each time the contacts 86(b)

operate until the detector 71, now connected to the bistable circuit 74, again operates and the cycle is repeated. Should the rate of charging be insufficient to reach the $\beta$ or $(\alpha+\beta)$ phase, the detector 73 operates and an adjustment to the time constant of the charge control circuit 78 can be made.

The apparatus of FIG. 8 is initially calibrated by adjusting, by means of zero and full scale adjustments of the measuring device, the response of the apparatus to solutions of known pH.

Figure 9:
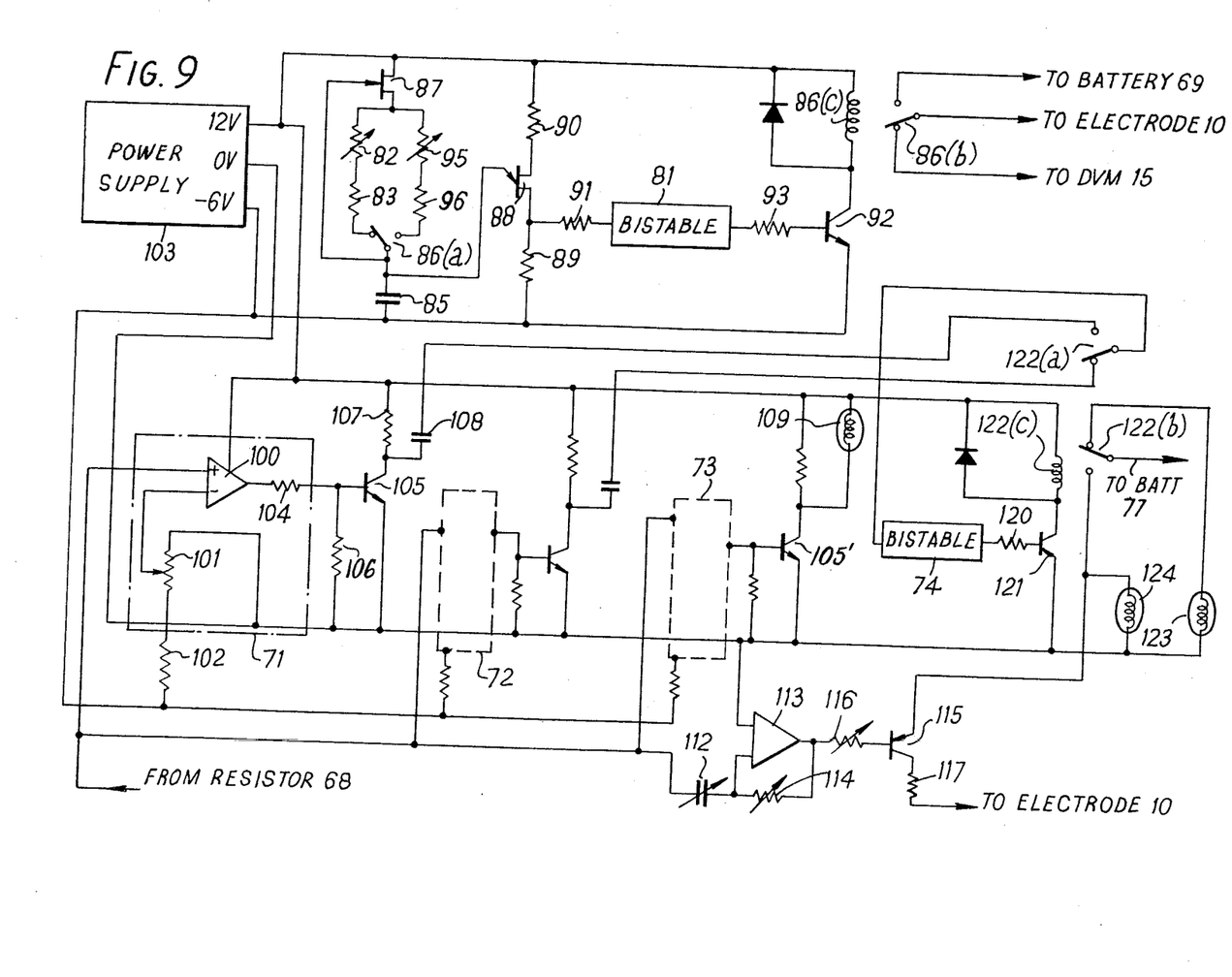
FIG. 9 is a part circuit diagram, part block diagram of the electrical control unit of FIG. 1.

The various circuits of FIG. 8 are shown in more detail in FIG. 9.

The timer 66 operates by charging and discharging a 100 $\mu$Farad capacitor 85. With the contacts 86($a$) of a relay in the position shown, the capacitor 85 charges through a type MRN5454 field effect transistor 87, a variable resistor 82 and 100 Kohm resistor 83 until it reaches a point where a type 2N2646 unijunction transistor 88 conducts discharging the capacitor 85 by way of a 100 ohm resistor 89. The voltage developed across this resistor is applied through a 10 Kohm resistor 91 to a bistable circuit 81. The transistor 88 has a 220 ohm base resistor 90.

The application of the puse to the bistable circuit switches on a BF156 transistor 92 by way of a 3.9 Kohm resistor 93 and thus current passes through the coil 86($c$) of a relay switching over the contacts 86($a$). Thus the capacitor now starts to charge through the FET 87 at a rate determined by variable potentiometer 95 and a 10 Kohm resistor 96. In this way the sequential timer circuit oscillates setting and resetting the bistable circuit 81 and in so doing operates the contacts 86($b$) of FIG. 8. The reset time of the circuit in the "measure" and "charge" states can be adjusted using the resistors 82 and 95.

Another form of timer which may be used is the NE555V timer chip integrated circuit.

The detector circuits 71, 72 and 73 each consist of the same basic circuit and for this reason only the detector 71 will be described in detail. A type LM710CN operational amplifier 100 is connected as a comparator, receiving the voltage from the resistor 68 at its non-inverting input. A reference voltage is applied to the non-inverting input from a 1 Kohm pre-set potentiometer 101 connected in series with a 4.7 Kohm resistor 102 connected to a $-6$ volt terminal of a power supply 103. Other voltages applied to the detectors are as shown in FIG. 9. The output of the comparator 100 is connected through a 1 Kohm resistor 104 to the base of a type BC108 transistor 105. A 100 Kohm base bias resistor 106 is connected between the base of the transistor 105 and the 0 volt rail of the power supply. A 1.5 Kohm resistor 107 is connected between the +12 volt rail and the power supply and the collector of the transistor 105 as a load resistor and the voltage developed across this load is coupled to the contacts 122($a$) by way of a 2,200 pF capacitor 108.

The detector 72 is coupled in the same way to the contacts 122($a$) but in the detector 73 the output of the transistor 105' is connected by way of a red warning light 109 to the 12 volt rail to indicate when rate of charge may be too low.

As an alternative to using three LM710CN operational amplifiers, two of these amplifiers may be replaced by a single SN72720 integrated circuit which includes two operational amplifiers.

In the circuit 78, the voltage across the resistor 68 is differentiated by a variable capacitor 112 and a type 741 operational amplifier 113 with a variable feedback resistor 114. The output of the amplifier 113 is applied to a transistor 115 by way of a variable resistor 116. This transistor and its emitter resistor 117 form the resistor 79 of FIG. 8. Thus the current passing between the electrodes 10 and 12 depends on the voltage applied to the base of the transistor 115 which is in turn determined by the differential of the voltage across the resistor 68.

The output of the bistable 74 is connected by way of a 3.9 Kohm resistor 120 to the base of a type D42C3 transistor 121. The collector of this transistor is connected to the coil 122($c$) of a relay which has the two sets of contacts already mentioned: 122($a$) and 122($b$). The contacts 122($a$) are connected at the input to the bistable circuit 74 to connect the output of either the detector 71 or the detector 72 in turn to the bistable circuit 74. The contacts 122($b$) are used to disconnect the battery 77 that is used to charge the palladium electrode when the detector 71 triggers. At the same time a lamp 123 is switched into circuit to indicate the hydrogen content of the palladium is sufficient for measurements. The contacts 122($b$) also switch in a lamp 124 when the detector 72 triggers to indicate that the palladium electrode is being charged with hydrogen.

If either of the lamps 123 or 124 is on measurements can proceed since the hydride is in the $(\alpha+\beta)$ phase, or just in the $\alpha$ or $\beta$ phase temporarily. When the lamp 109 is on measurements should not proceed.

In FIG. 8 the battery 77 and the switch 80 may be replaced by a pulse generator which provides both negative charging pulses and positive cleaning pulses each time the contacts 122($b$) are closed. The pulse rate required for cleaning depends on the amount of cleaning necessary and therefore on the electrolyte. Usually positive pulses at a rate of between one every second and one every several minutes will be sufficient. These pulses in addition to replacing hydrogen and cleaning the electrode, also remove oxygen and remove reducible ions in the way described above.

Alternatively, a manual switch (not shown) may be inserted in series with the battery 77 to allow charging to be carried out, when the lamp 124 lights, as a series of pulses generated manually by intermittent operation of the switch.

With the arrangement of FIG. 8 should the detector 73 and the lamp 109 indicate that the rate of charging is insufficient the capacitor 112 and the resistor 114 can be varied to increase the rate of charge by varying the time constant of the differentiating circuit. Means may however be provided to carry out this variation automatically in dependence upon the output of the detector 73.

Although some embodiments of the invention have been specifically described it will be apparent that the invention can be put into practice in many other ways. For example, as has been mentioned, the electrodes of FIGS. 4 and 5 may be operated in the $\beta$ phase and this is useful where a zero electrode potential is required. For a given electrode potential the range of hydrogen concentration is comparatively small and therefore the hydrogen concentration has to be carefully controlled. The potential between the cylinder 38 and the electrode 10 allows precise control but different settings for the voltages at which the detectors 71, 72 and 73 operate are required. Instead a different detector circuit arrangement may, as with the other electrodes described, be used.

I claim:

1. Apparatus for use in measuring the concentration of a particular ion in a liquid, comprising:
   an ion selective electrode which includes a metal capable of forming a hydride,
   supply means for supplying hydrogen to the metal, the supply means being constructed to supply hydrogen, when the ion selective electrode is in contact with an electrolyte the ion concentration of which is to be measured, by electrolysis of the said electrolyte,
   monitoring means for determining the concentration of hydrogen in the metal by monitoring a hydrogen concentration-related property of the metal and for providing an output signal dependent on the said concentration of hydrogen, and
   control means for automatically controlling the times at which electrolysis is carried out by the supply means at least partially in accordance with the output signal of the monitoring means to maintain, when the ion sensitive electrode is in the said electrolyte, the said concentration of hydrogen in the metal within a predetermined range such that the electrode potential remains constant when measured in a solution having a constant concentration of the said particular ion.

2. Apparatus according to claim 20 wherein the ion selective electrode includes a metal hydride of the said metal.

3. Apparatus according to claim 2 wherein the monitoring means is adapted to measure the electrical resistance of the metal hydride of the said electrode.

4. Apparatus according to claim 21 including a further electrode and wherein the control means includes means for applying electrical pulses, at times, between the ion selective electrode and the further electrode, the ion selective electrode being made positive with respect to the further electrode during said pulses.

5. Apparatus according to claim 21 including
   a reference electrode and,
   measuring means for providing a signal indicative of the potential between the ion sensitive electrode and the reference electrode,
   the control means alternately coupling the monitoring means and the measuring means for monitoring and measuring, respectively.

6. Apparatus according to claim 2, wherein the control means includes means for providing intervals for electrode potential measurement in which electrolysis is not carried out and for providing intervals in which electrolysis may be carried out if the said concentration of hydrogen is outside the said range.

7. Apparatus according to claim 2 wherein said metal is selected from the group consisting of palladium, yttrium, zirconium, titanium, vanadium and alloys thereof.

8. Apparatus according to claim 1 including an inert hollow elongated body with palladium wire forming the ion selective electrode wound round the outside of the body.

9. Apparatus according to claim 8 including
   a reference electrode within the elongated body and porous connecting means between the interior and exterior of the said body.

10. Apparatus for use in measuring the concentration of a particular ion in a liquid, comprising:
    an ion selective electrode which includes a metal capable of forming a hydride,,
    supply means for supplying hydrogen to the metal, while the ion sensitive electrode is in contact with an electrolyte, from a hydrogen source remote from that part of the ion selective electrode which is in contact with the electrolyte, to cause, in operation, a metal hydride to be formed,
    monitoring means for determining the concentration of hydrogen in the metal by monitoring a hydrogen concentration-related property of the metal and for providing an output signal dependent on the said concentration of hydrogen, and
    control means for automatically controlling the supply of hydrogen to the metal in accordance with the output signal of the monitoring means to maintain the said concentration of hydrogen in the metal within a predetermined range such that the electrode potential remains constant when measured in a solution having a constant concentration of the said particular ion.

11. Apparatus according to claim 10 including a metal hydride of the said metal.

12. Apparatus according to claim 11 wherein the monitoring means is adapted to measure the electrical resistance to the metal hydride of the said electrode.

13. Apparatus according to claim 11 including
    a reference electrode,
    measuring means for providing a signal indicative of the potential between the ion sensitive electrode and the reference electrode,
    the control means alternately coupling the monitoring means and the measuring means for monitoring and measuring, respectively.

14. Apparatus according to claim 10 wherein the supply means includes electrolytic means for generating hydrogen by electrolysis.

15. Apparatus according to claim 3 including an inert hollow elongated body with palladium wire forming the ion selective electrode wound round the outside of the body and extending to the interior thereof, and an auxiliary electrode within the body, whereby when the hollow body contains electrolyte the palladium wire can be charged with hydrogen by electrolysis between the palladium wire and the auxiliary electrode.

16. Apparatus according to claim 10 wherein the metal of the ion sensitive electrode is in the form of a tube with one end sealed and the other end adapted to be connected to the supply means to allow hydrogen to reach the interior of the tube.

17. Apparatus for use in measuring the concentration of a particular ion in a liquid, comprising:
    an ion selective electrode which includes a metal capable of forming a hydride, the metal selected from the group consisting of palladium, yttrium, zirconium, titanium, vanadium, and alloys thereof,
    supply means for supplying hydrogen to the metal, while the ion sensitive electrode is in contact with an electrolyte, from a hydrogen source remote from that part of the ion selective electrode which is in contact with the electrolyte, to cause, in operation, a metal hydride to be formed,
    monitoring means for determining the concentration of hydrogen in the metal by monitoring a hydrogen concentration-related property of the metal and for providing an output signal dependent on the said concentration of hydrogen, and
    control means for automatically controlling the supply of hydrogen to the metal in accordance with the output signal of the monitoring means to maintain the said concentration of hydrogen in the metal within a predetermined range such that the electrode potential remains constant when measured in a solution having a constant concentration of the said particular ion, 18. Apparatus for measuring the concentration of hydrogen ions in a liquid, comprising:

an ion selective electrode which includes a metal capable of forming a hydride, said metal selected from the group consisting of palladium, yttrium, zirconium, titanium, vanadium and alloys thereof, supply means for supplying hydrogen to the metal, the supply means being constructed to supply hydrogen, when the ion selective electrode is in contact with an electrolyte the ion concentration of which is to be measured, by electrolysis of the said electrolyte, monitoring means for determining the concentration of hydrogen in the metal by monitoring a hydrogen concentration-related property of the metal and for providing an output signal dependent on the said concentration of hydrogen, and control means for automatically controlling the times at which electrolysis is carried out by the supply means at least partially in accordance with the output signal of the monitoring means to maintain, when the ion sensitive electrode is in the said electrolyte, the said concentration of hydrogen in the metal within a predetermined range such that the electrode potential remains constant when measured in a solution having a constant concentration of the said particular ion.

* * * * *

UNITED STATES PATENT AND TRADEMARK OFFICE
CERTIFICATE OF CORRECTION

PATENT NO. : 4,242,189
DATED : December 30, 1980
INVENTOR(S) : John V. DOBSON

It is certified that error appears in the above-identified patent and that said Letters Patent are hereby corrected as shown below:

In the heading:

The patent should be read as containing the following information:

[30]  Foreign Application Priority Data

July 18, 1973    Great Britain......34132/73

Signed and Sealed this

Twenty-third Day of June 1981

[SEAL]

Attest:

RENE D. TEGTMEYER

*Attesting Officer*    *Acting Commissioner of Patents and Trademarks*